(12) United States Patent
Shieh

(10) Patent No.: US 9,241,668 B2
(45) Date of Patent: Jan. 26, 2016

(54) PERIPHERAL PHYSIOLOGY INSPECTION APPARATUS AND PERIPHERAL AUXILIARY APPARATUS OF SMART PHONE

(75) Inventor: Dar-Bin Shieh, Tainan (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 1115 days.

(21) Appl. No.: 13/290,217

(22) Filed: Nov. 7, 2011

(65) Prior Publication Data

US 2012/0116184 A1 May 10, 2012

Related U.S. Application Data

(60) Provisional application No. 61/410,509, filed on Nov. 5, 2010.

(51) Int. Cl.
| | |
|---|---|
| *A61B 5/00* | (2006.01) |
| *A61B 5/01* | (2006.01) |
| *A61B 5/0404* | (2006.01) |
| *A61B 5/1455* | (2006.01) |
| *H04M 1/00* | (2006.01) |
| *H04M 1/05* | (2006.01) |
| *H04M 1/725* | (2006.01) |

(52) U.S. Cl.
CPC ............... *A61B 5/6817* (2013.01); *A61B 5/01* (2013.01); *A61B 5/0404* (2013.01); *A61B 5/14552* (2013.01); *A61B 5/682* (2013.01); *A61B 2560/045* (2013.01); *H04M 1/05* (2013.01); *H04M 1/72527* (2013.01)

(58) Field of Classification Search
CPC ............. A61B 5/0404; A61B 5/14552; A61B 5/6817; A61B 5/02433; A61B 5/14542; H04M 1/72527; H04M 1/72519; H04M 1/6058; G01J 5/0011
See application file for complete search history.

(56) References Cited

U.S. PATENT DOCUMENTS

| | | | |
|---|---|---|---|
| 2004/0225207 A1* | 11/2004 | Bae et al. ..................... | 600/340 |
| 2006/0045304 A1* | 3/2006 | Lee et al. ..................... | 381/384 |
| 2010/0054493 A1* | 3/2010 | Lin et al. ..................... | 381/74 |
| 2010/0217100 A1* | 8/2010 | LeBoeuf et al. ............. | 600/301 |

FOREIGN PATENT DOCUMENTS

CN 1788674 A 6/2006

* cited by examiner

*Primary Examiner* — William Thomson
*Assistant Examiner* — Marie Archer
(74) *Attorney, Agent, or Firm* — Bacon & Thomas, PLLC

(57) ABSTRACT

A peripheral physiology inspection apparatus of smart phone is connected with a smart phone having a TRRS socket for performing a physiology inspection. The peripheral physiology inspection apparatus includes: an inspection main body including a first physiology sensing unit; a plurality of signal transmission units; and a TRRS terminal for connecting with the inspection main body via the signal transmission units. The TRRS terminal is corresponding to the TRRS socket for allowing the inspection main body to be electrically connected to the smart phone, thereby enabling the smart phone to analyze and process physiology signals inspected by and delivered from the inspection main body.

2 Claims, 11 Drawing Sheets

PERIPHERAL PHYSIOLOGY INSPECTION APPARATUS AND PERIPHERAL AUXILIARY APPARATUS OF SMART PHONE

CROSS REFERENCE TO RELATED APPLICATION

This application claims the benefit of filing date of U.S. Provisional Application Ser. No. 61/410,509, entitled "Earphone sensor design for smart phone" filed Nov. 5, 2010 under 35 USC §119(e)(1).

BACKGROUND OF THE INVENTION

1. Field of the Invention

The present invention relates to a peripheral physiology inspection apparatus and a peripheral auxiliary apparatus of smart phone and, more particularly, to a peripheral physiology inspection apparatus and a peripheral auxiliary apparatus of smart phone capable of connecting with a smart phone, and integrating with multiple physiology sensing units for inspecting body temperature, oximetry, heart rhythm status, or electroencephalogram.

2. Description of Related Art

With the change of diet behavior and life style, and the aging of population, more and more people are unable to take health examination in a hospital regularly, and thus the demand on home healthcare increases rapidly. Accordingly, it is desirable to develop a simple home physiology inspection apparatus for providing a simple and effective healthcare at home, so as to promote the health condition for modern people by long-term health tracing.

Various kinds of home medical inspection apparatus has been developed in the market for inspecting an inspector's physiology signal, such as temperature, heartbeat frequency, pulse, etc., so as to ascertain the inspector's health condition with the assistance of those physiology signals. In the physiology signals, electrocardiography (EKG) can be used as a tool for inspecting an inspector's heart health condition. The voltage difference of a heart is reflected to the surface of a human body by the tissue and the body fluid surrounding the heart. Moreover, electroencephalography (EEG) can be used as a tool for inspecting an inspector's cerebrum status, by measuring the potential difference between two contacts on the head of a human body, thereby allowing people to realize the cerebrum status and to diagnose diseases with regard to cerebrum. However, these medical inspection apparatuses are so expensive and thus are not available to healthcare at home. As a result, it is unable to efficiently take care of patients who need healthcare at home.

Therefore, if a medical inspection apparatus capable of being operated effortlessly can be developed, the implementation on popularized healthcare at home may then be achieved. By this, most of the people can trace various physiology signals by themselves through the home medical inspection apparatus, so as to advance the monitoring on health condition and to increase the management efficiency.

SUMMARY OF THE INVENTION

An object of the present invention is to provide a peripheral physiology inspection apparatus of smart phone, which is connected with a smart phone for performing physiology inspection. The peripheral physiology inspection apparatus of smart phone can carry multiple physiology inspection units thereon for users to inspect their physiology signal such as body temperature, oximetry, heart rhythm status, or electroencephalogram.

To achieve the object, the peripheral physiology inspection apparatus of smart phone is connected with a smart phone having a TRRS socket for performing a physiology inspection. The peripheral physiology inspection apparatus comprises: an inspection main body including a first physiology sensing unit; a plurality of signal transmission units; and a TRRS terminal for connecting with the inspection main body via the signal transmission units. The TRRS terminal is corresponding to the TRRS socket for allowing the inspection main body to be electrically connected to the smart phone, thereby enabling the smart phone to analyze and process physiology signals inspected by and delivered from the inspection main body.

It is noted that the aforesaid TRRS terminal preferably comprises four regions, which are Tip, Ring, Ring, and Sleeve. These four regions are respectively in charge of a transmission for left sound track, a transmission for right sound track, a transmission for microphone audio, and the reset one for connecting to ground.

Furthermore, in a first preferred embodiment, the peripheral physiology inspection apparatus of smart phone of the present invention preferably further comprises a signal conversion interface disposed preferably between the inspection main body and the smart phone, for converting the physiology signal inspected by the inspection main body into an audio signal, so as to allow the smart phone to receive the audio signal through the TRRS socket. Moreover, the smart phone preferably performs decoding or signal processing to the audio signal, wherein the decoding process is preferably to be amplitude, frequency, or digital encoding/decoding.

Moreover, in a second preferred embodiment, the peripheral physiology inspection apparatus of smart phone of the present invention preferably further comprises a second physiology sensing unit, and an electrode plate is preferably disposed on the second physiology sensing unit. Additionally, the signal conversion interface as mentioned in the first preferred embodiment is also included in the present second embodiment as well. Further, the second physiology sensing unit is preferably disposed on a switch. The switch is provided for performing a switching mechanism, and the switching mechanism is preferably controlled by sound form a microphone and through a logic circuit. In addition, the first and the second physiology sensing units are preferably connected with each other by the signal transmission in the present second embodiment.

Besides, in a third preferred embodiment, the aforementioned first physiology sensing unit is an earphone-type physiology sensing unit comprising: at least one earphone main body; a conductive surface disposed on the earphone main body; and a temperature-sensing element disposed in the earphone main body for sensing a body temperature of ear cavity of a human body. The temperature-sensing element is not limited to any sorts of temperature-sensing element. However, the temperature-sensing element is preferably a thermistor, a thermal resistor, a thermal coupler, a thermal IC, a P/N junction, or an infrared temperature-sensing element. Furthermore, in the present third preferred embodiment, the conductive surface is a conductive rubber, a conductive silicon gel, or an electrode interface, which is integrated with the earphone main body. The conductive surface is preferably to be an electrode sheet or an electrode ring.

It is noted that the number of the earphone main body is preferably to be two in the present third preferred embodiment, and the two earphone main bodies are preferably disposed to the left and the right ear of a user. By the measurement between the two electrodes, where one for the conductive surface of the earphone main body disposed to the left and the right ear of a user and the other for the electrode plate of the second physiology sensing unit, the EKG of a user can be inspected and is then amplified for acquiring enhanced EKG. Preferably, the EEG of a user is inspected through the electrodes between the left and the right ear.

Then, in a fourth preferred embodiment, the aforementioned first physiology sensing unit is an earphone-type physiology sensing unit comprising: at least one earphone main body; a light emitting element disposed on the earphone main body for emitting a reference light; and a light receiving element disposed on the earphone main body for receiving the reference light reflected by ear cavity skin of a human body. The form of the aforesaid light emitting element is not limited. However, the light emitting element is preferably a pulse oximetry LED, and the light receiving element is preferably a light sensor. In addition, the pulse oximetry LED preferably emits 2-3 light sources with different wavelength for increasing the accuracy of the peripheral physiology inspection apparatus of the fourth preferred embodiment. Besides, the aforementioned 2-3 light sources with different wavelength preferably include infrared and near infrared.

Moreover, in a fifth preferred embodiment, the aforementioned first physiology sensing unit is an earphone-type physiology sensing unit comprising: at least one earphone main body defined therein a channel space; an infrared transparent drum membrane disposed inside the earphone main body and facing to the channel space; and an NIR sensing element disposed inside the earphone main body and facing to the channel space through the infrared transparent drum membrane. Additionally, the earphone-type physiology sensing unit preferably further comprises an optical fiber for allowing the overall design of the peripheral physiology inspection apparatus in accordance with the fifth preferred embodiment to be smaller and more aesthetic, and the optical fiber is preferably connected to the earphone main body and the NIR sensing element.

Furthermore, in a sixth preferred embodiment, the aforementioned second physiology sensing unit is an oral-type physiology sensing unit. The shape of the oral-type physiology sensing unit is not limited, but the shape of the oral-type physiology sensing unit is preferably be heart shape so as to prettify the appearance of the peripheral physiology inspection apparatus of smart phone in accordance with the present sixth preferred embodiment. The aforesaid second physiology sensing unit preferably further comprises at least one auxiliary element and the shape thereof is not limited. However, the shape of the auxiliary element is preferably to be wing shape, so as to allow a user to hold the peripheral physiology inspection apparatus in mouth easily by biting the auxiliary element and further to increase the aesthetic appearance of the peripheral physiology inspection apparatus.

Besides, in a seventh preferred embodiment, the aforementioned peripheral physiology inspection apparatus preferably comprises a terminal receiver for connecting to the inspection main body via the signal transmission units. Moreover, the aforementioned peripheral physiology inspection apparatus preferably comprises an accommodation element for allowing the peripheral physiology inspection apparatus to form a closed shape. This closed shape of peripheral physiology inspection apparatus with the accommodation element can be put onto a hand of a user, allowing the user to take out conveniently.

Additionally, in an eighth preferred embodiment, the aforesaid earphone-type physiology sensing unit preferably further comprises a carotid artery sensing element. The earphone-type physiology sensing unit is preferably disposed to the left ear of a user, and the carotid artery sensing element is preferably connected to the carotid artery of the user. Therefore, it helps for measuring or inspecting the EKG and the EEG of a user, and the overall design of the peripheral physiology inspection apparatus is also made to be aesthetic.

Please note that the features described in each preferred embodiment are not limited to be implemented in the particular embodiments. Those skilled in the art may combine the features as suggested in the above embodiments arbitrarily based on their requirements for performing different physiology signal inspections.

Additionally, EKG is easily interfered by external noise (such as electromagnetic wave from a mobile phone) or background noise (such as circuit noise). Thus, in the aforementioned preferred embodiments, when inspecting the EKG, it is preferred to adjust the contact positions of the two contacts, for allowing the heart of the user to be in between the two electrode contacts. By this, a stronger EKG signal is acquired and the efficiency of EKG inspection is then increased.

The spirit of the present invention is to integrate a physiology inspection apparatus and a smart phone, wherein the physiology inspection apparatus and the smart phone are connected through a TRRS terminal.

Based on the above spirit, the integration of the physiology inspection apparatus with an earphone is further popularized by the present invention, for promoting the convenience of users. Furthermore based on the above spirit, turning the physiology inspection apparatus of the present invention into a necklace-type, or into a bracelet-type physiology inspection apparatus is further popularized by the present invention, for promoting the convenience of users.

Another object of the present invention is to provide a peripheral auxiliary apparatus of smart phone for use with a smart phone. The peripheral auxiliary apparatus of smart phone is integrated with a smart phone for allowing the smart phone to be connected with an arbitrary peripheral physiology inspection apparatus so as to inspect temperature, oximetry, heart rhythm status, electroencephalogram or other physiology signal.

To achieve the object, the peripheral auxiliary apparatus of smart phone is provided for use with a smart phone having a TRRS socket. The peripheral auxiliary apparatus comprises: a shell having a receiving part for receiving the smart phone, a TRRS terminal, and a TRRS terminal receiver; a battery unit disposed inside the shell; a power management unit electrically connected to the battery unit; a first conductive unit disposed on the shell; a second conductive unit disposed on the shell for contacting the first conductive unit correspondingly, the second conductive unit being electrically connected to the power management unit; and a signal conversion unit disposed in the shell and electrically connected to the first conductive unit, wherein the TRRS terminal and the TRRS terminal receiver are electrically connected with the signal conversion unit, and the TRRS terminal is inserted into the TRRS socket of the smart phone correspondingly.

Please note that the battery unit is not limited to any sorts of battery. Any battery with properties of high energy-storing efficiency, tiny volume is suitable for the peripheral auxiliary apparatus of smart phone of the present invention. However, the battery unit is preferably a Li-polymer battery.

Besides, the aforementioned shell further includes a connection port, and the connection port is preferably a 30-pin connection port. The connection port corresponds to a connection port of a smart phone when the smart phone is received in the receiving part correspondingly, thereby allowing the connection port of the shell and the connection port of the smart phone to be electrically connected with each other.

Moreover, the aforementioned shell further includes an USB connection port. The USB connection port is preferably a mini-A type USB connection port or a mini-B type USB connection port, and the USB connection port of the smart phone preferably corresponds to the a USB connection port of a smart phone. Therefore, when the smart phone is received in the shell, the shell may block the USB connection port of a smart phone, and such a problem can be solved by providing the USB connection port of the shell. In addition, the shell further includes an upper shell and a lower shell, and the upper and lower shells are preferably integrated together correspondingly to form the receiving part.

Other objects, advantages, and novel features of the invention will become more apparent from the following detailed description when taken in conjunction with the accompanying drawings.

DETAILED DESCRIPTION OF THE PREFERRED EMBODIMENT

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

Embodiment 1

Figure 1:
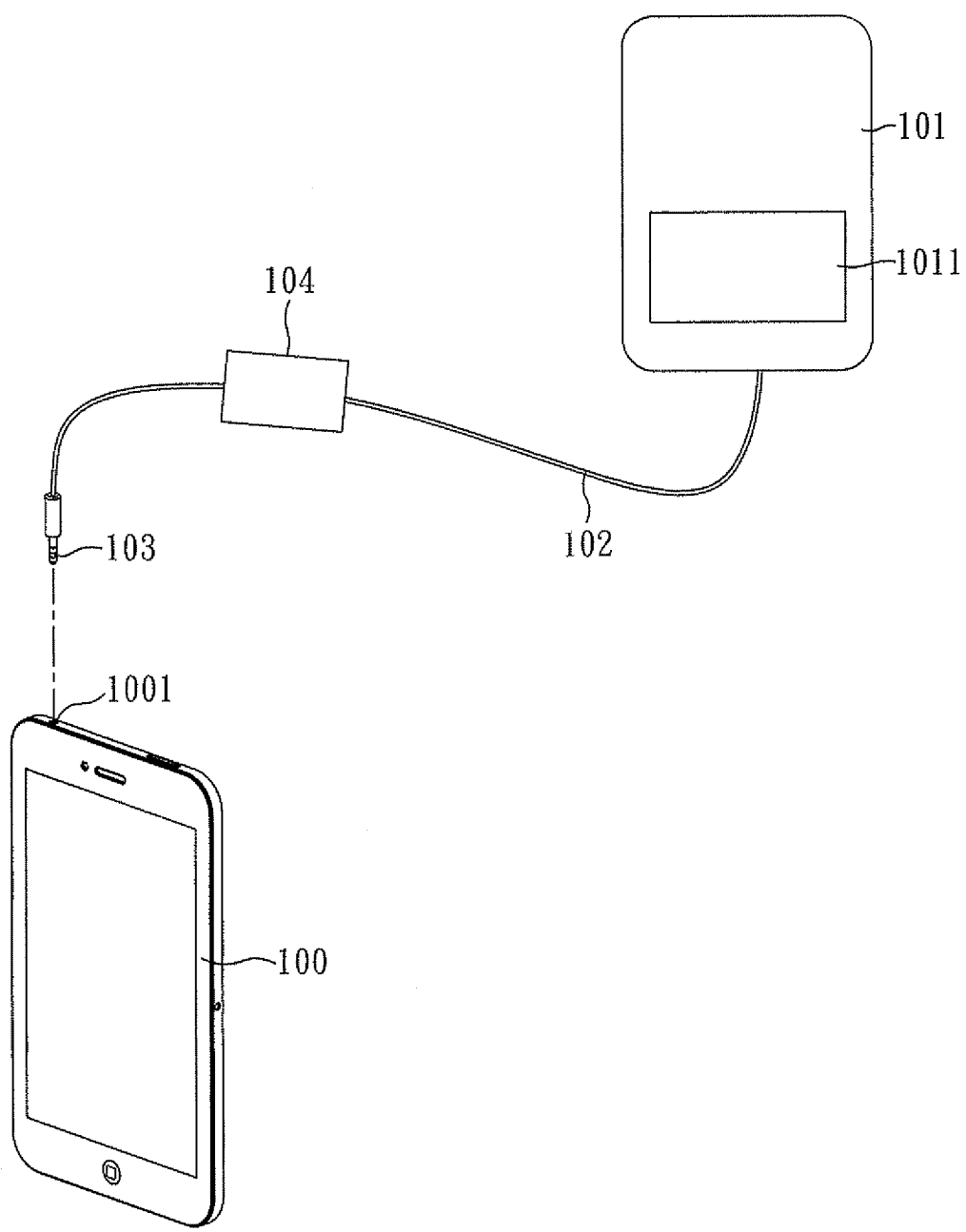
FIG. 1 is a schematic view illustrating the peripheral physiology inspection apparatus of smart phone in accordance with the first embodiment of the present invention.

With reference to FIG. 1, FIG. 1 is a schematic view illustrating the peripheral physiology inspection apparatus of smart phone in accordance with the first embodiment of the present invention. As shown in FIG. 1, the peripheral physiology inspection apparatus of smart phone is adapted to be connected with a smart phone 100 having a TRRS (Tip-Ring-Ring-Sleeve) socket 1001 for performing a physiology inspection. The smart phone is, for example, an iPhone. The peripheral physiology inspection apparatus includes: an inspection main body 101, a plurality of signal transmission units 102, and a TRRS terminal 103.

Furthermore, the inspection main body 101 includes a first physiology sensing unit 1011, and the TRRS terminal 103 corresponds to the TRRS socket 1001 for allowing the inspection main body 101 to be electrically connected to the smart phone 100, thereby enabling the smart phone 100 to analyze and process physiology signals inspected by and delivered from the inspection main body 101 through the signal transmission units 102.

It is noted that the peripheral physiology inspection apparatus of smart phone in accordance with the first embodiment of the present invention may further include a signal conversion interface 104, and this signal conversion interface 104 is disposed between the inspection main body 101 and the smart phone 100. The signal conversion interface 104 is provided for converting the physiology signal inspected by the inspection main body 101 into an audio signal, so as to allow the smart phone 100 to receive the audio signal through the TRRS socket 1001.

It is noted that the aforementioned TRRS terminal includes four regions of Tip, Ring, Ring, and Sleeve, and these four regions are respectively in charge of a transmission for left sound track, a transmission for right sound track, a transmission for microphone audio, and a ground region. The implementation of TRRS terminal is well known to those skilled in the art and thus a detailed description is deemed unnecessary.

With the above description, it is known that the physiology signal inspected by the inspection main body 101 is not necessary to be a signal in audio format. Thus, the physiology signal is delivered to the signal conversion interface 104 for being converted into an audio signal. As a result, the audio signal after conversion can be sent to the smart phone 100 via the TRRS terminal 103 for further proceeding with a decoding process or other signal processing by the smart phone 100, wherein the decoding process can be amplitude, frequency, or digital encoding/decoding.

Embodiment 2

Figure 2A:
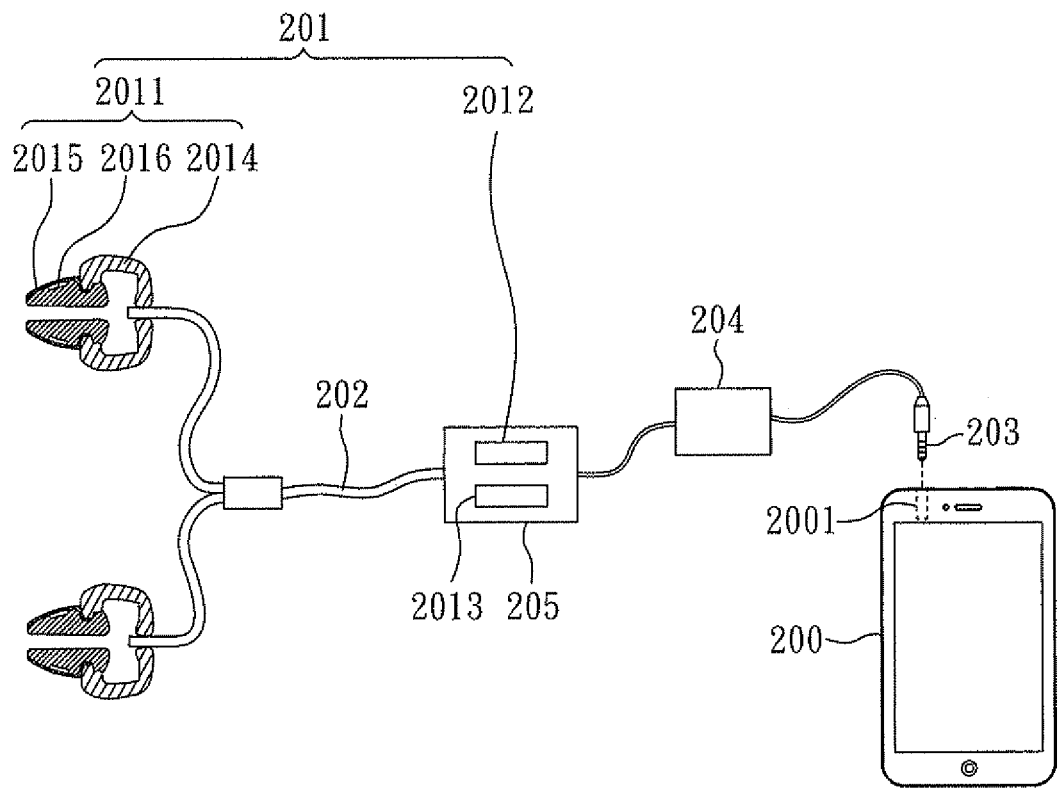
FIG. 2A is a schematic view illustrating the peripheral physiology inspection apparatus of smart phone in accordance with the second embodiment of the present invention.

With reference to FIG. 2A, FIG. 2A is a schematic view illustrating the peripheral physiology inspection apparatus of smart phone in accordance with the second embodiment of the present invention. As shown in FIG. 2A, the peripheral physiology inspection apparatus of smart phone is adapted to be connected with a smart phone 200 having a TRRS socket 2001 for performing a physiology inspection. The peripheral physiology inspection apparatus includes: an inspection main body 201, a plurality of signal transmission units 202, and a TRRS terminal 203.

Furthermore, the inspection main body 201 includes a first physiology sensing unit 2011, and the TRRS terminal 203 corresponds to the TRRS socket 2001 for allowing the inspection main body 201 to be electrically connected to the smart phone 200, thereby enabling the smart phone 200 to analyze and process physiology signals inspected by and delivered from the inspection main body 201 through the signal transmission units 202.

It is noted that the peripheral physiology inspection apparatus of smart phone in accordance with the second embodiment of the present invention may further include a signal conversion interface 204, and this signal conversion interface 204 is disposed between the inspection main body 201 and the smart phone 200. The signal conversion interface 204 is is provided for converting the physiology signal inspected by the inspection main body 201 into an audio signal, so as to allow the smart phone 200 to receive the audio signal through the TRRS socket 2001.

Moreover, in the peripheral physiology inspection apparatus of smart phone in accordance with the second embodiment of the present invention, the inspection main body 201 further includes a second physiology sensing unit 2012, and an electrode plate 2013 is disposed on the second physiology sensing unit 2012. The second physiology sensing unit 2012 is disposed on a switch 205. Besides, the first physiology sensing unit 2011 and the second physiology sensing unit 2012 are connected with each other by the signal transmission units 202. The switch 205 is provided for performing a switching mechanism, and the switching mechanism is preferably controlled by sound form a microphone and through a logic circuit.

It is also noted that, in the peripheral physiology inspection apparatus of smart phone in accordance with the second embodiment of the present invention, the first physiology sensing unit 2011 is an earphone-type physiology sensing unit as shown in FIG. 2A. The earphone-type physiology sensing unit includes: an earphone main body 2014; a conductive surface 2015, and a temperature-sensing element 2016.

Additionally, the aforementioned conductive surface 2015 can be a conductive rubber, a conductive silicon gel, or an electrode surface, such as an electrode sheet or a electrode ring, integrated with the earphone main body 2014. In this embodiment, the conductive surface 2015 is an electrode sheet, disposed on the earphone main body 2014. The temperature-sensing element 2016 is disposed in the earphone main body 2014 for sensing a body temperature of ear cavity of a human body. The temperature-sensing element is preferably a thermistor, a thermal resistor, a thermal coupler, a thermal IC, a P/N junction, or an infrared temperature-sensing element. In this embodiment, temperature-sensing element 2016 is a thermal resistor.

Besides, the aforementioned conductive surface 2015 can be a metal conductive film or a non-metal conductive film. In this embodiment, the conductive surface 2015 is a metal conductive film. The quantity of the earphone main body 2014 is at least to be one and, in this embodiment, there are two earphone main bodies. Moreover, these two earphone main bodies 2014 are adapted to be disposed in the left and the right ear of a user. The EKG of a user can thus be inspected via the sensing between the two electrodes, one for the conductive surface 2015 of the earphone main body 2014 disposed in the user's right ear and the other for the electrode plate 2013 of the second physiology sensing unit 2012, and the EKG can be further amplified. The user's EEG can be inspected by the sensing between the electrodes of the right and the left ears.

As demonstrated in the first embodiment of the present invention, a TRRS terminal includes four regions of Tip, Ring, Ring, and Sleeve, which are respectively in charge of a transmission for left sound track (the region is abbreviated as left sound track audio region hereinafter), a transmission for right sound track (the region is abbreviated as right sound track audio region hereinafter), a transmission for microphone audio (the region is abbreviated as microphone audio region hereinafter), and a ground region. Moreover, the aforementioned switch 205 is provided for a user to switch the peripheral physiology inspection apparatus of smart phone for measuring the temperature or the EKG, or for acting as a typical earphone microphone to listen to music and receive audio signal. The switching as mentioned above can be performed electrically; i.e., the switching command is issued by user's speaking or operating the smart phone. The principles for temperature inspection and EKG inspection are respectively demonstrated as follows.

Temperature Inspection

When a user switches the peripheral physiology inspection apparatus of smart phone in accordance with the second embodiment of the present invention for temperature inspection, the switch 205 connects the temperature-sensing element 2016 and the microphone audio region of the TRRS terminal electrically.

Then, the temperature-sensing element 2016 senses the temperature of the ear cavity of the user to acquire a temperature physiology signal. After that, the temperature physiology signal is delivered to the signal conversion interface 204 through the signal transmission unit 202 and, after the signal conversion interface 204 has received the temperature physiology signal, the temperature physiology signal is converted into an audio signal. Therefore, the audio signal can be sent to the smart phone 200 for analysis via the TRRS terminal.

It is noted that the microphone audio region of the TRRS terminal is occupied at this moment by the temperature-sensing element 2016. Hence, an encoding/decoding process should be applied if the user would like to speak through the microphone while inspecting temperature. Moreover, the smart phone 200 can still transmit audio signal to earphone since the regions in charge of left and right sound track transmissions are not occupied. Thus, the user can listen to music and demonstrate temperature inspection at the same time, and further issue command (such as voice command) for vocal physiology monitoring broadcasts.

EKG Inspection

When a user switches the peripheral physiology inspection apparatus of smart phone in accordance with the second embodiment of the present invention for EKG inspection, the switch 205 connects the microphone audio region of the TRRS terminal and the sensing signal generated by the conductive surface 2015 after being filtered, amplified and encoded.

Additionally, a first contact is formed due to the touching between the conductive surface 2015 of the earphone main body 2014 and the skin inside the ear cavity of the user. Furthermore, the user holds the second physiology sensing unit 2012 by hand, and thus a second contact is formed due to the touching between the electrode plate 2013 and the skin of the user's hand, thereby forming an inspection loop. It is noted that the second physiology sensing unit 2012 is not limited to be held by hand. The user can clamp the second physiology sensing unit 2012 beneath the armpit of the user, or use a fixer to hold the second physiology sensing unit 2012 for touching the arm of the user thereby making the second contact, or to make the second contact by touching the skin on human body in any other manner.

After the inspection loop is formed, heartbeat status of the user can be measured by the peripheral physiology inspection apparatus of smart phone in accordance with the second embodiment of the present invention. This physiology signal of heartbeat status is then sent to the signal conversion interface 204 via the signal transmission unit 202 for being converted into an audio signal, which is then delivered to the smart phone 200 through the TRRS terminal for analysis, so as to acquire the user's EKG.

As described previously, the electrode plate 2013 of the second physiology sensing unit 2012 occupies the microphone audio region or one of the left and right sound track audio regions. If the microphone audio region is occupied, the user is unable to speak through the microphone when EKG inspection is selected, and the temperature and the EKG inspections cannot be performed at the same time. However, audio signal can still be delivered from smart phone 200 to earphone since the left and the right sound track audio regions are not occupied, so that listing to music and EKG inspection can be performed at the same time.

Additionally, EKG signal is likely to be interfered by external noise (such as electromagnetic wave from a mobile phone), or background noise (such as circuit noise). Thus, it is better to adjust the contacting positions of the first and the second contacts, for allowing the heart of the user to be in between the two electrode contacts. By this, a stronger EKG signal is acquired and the efficiency of EKG inspection is then increased.

Figure 2B:
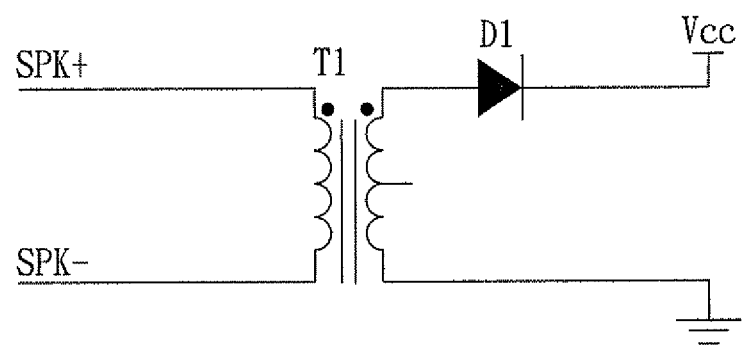
FIG. 2B is a schematic view illustrating the power supply unit used for the peripheral physiology inspection apparatus of smart phone in accordance with the second embodiment of the present invention.

With reference to FIG. 2B, FIG. 2B is a schematic view illustrating the power supply unit used for the peripheral physiology inspection apparatus of smart phone in accordance with the second embodiment of the present invention. The power supply unit is electrically connected with part of the earphone regions under a charging mode. To be more specific, the first end SPK+ and the second end SPK− of the power supply unit are connected with the left sound track audio region and the right sound track audio region respectively, for receiving a sinusoid wave provided by the smart phone. The sinusoid wave is then converted by a transformer (for example, T1 as illustrated in FIG. 2B), and provided to the peripheral physiology inspection apparatus and a power storage unit.

It is noted that the power supply unit may further include a capacitor (not shown) for storing extra electric energy, wherein the capacitor is preferred to be a micro capacitor (such as a thin film capacitor) or a super capacitor. Moreover, the transformer T1 and the rectifier diode as shown in FIG. 2B are preferably a micro transformer and a micro rectifier diode (such as thin film transformer and thin film rectifier diode).

Embodiment 3

The peripheral physiology inspection apparatus of smart phone in accordance with the third embodiment of the present invention is similar to that in accordance with the second embodiment, except for the structure of the first physiology sensing unit. The first physiology sensing unit in the peripheral physiology inspection apparatus of smart phone in accordance with the third embodiment of the present invention is an earphone-type physiology sensing unit.

Figure 3:
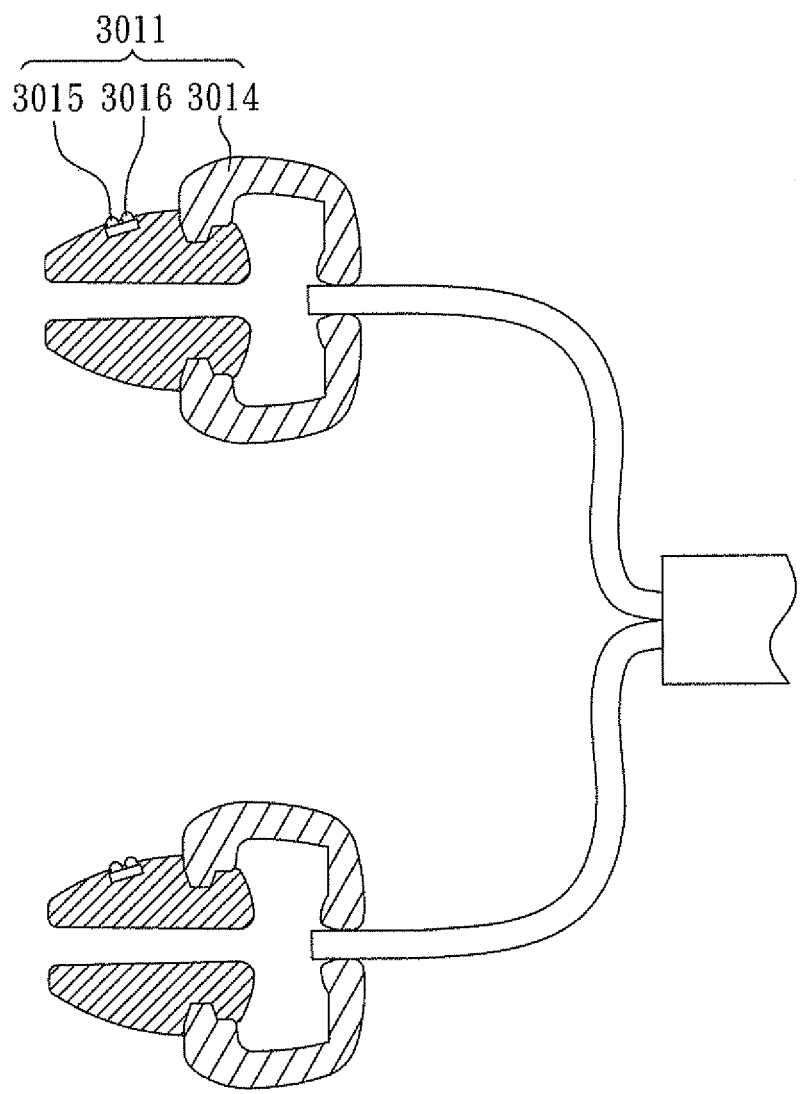
FIG. 3 is a schematic view illustrating the peripheral physiology inspection apparatus of smart phone in accordance with the third embodiment of the present invention.

With reference to FIG. 3, FIG. 3 is a schematic view illustrating the peripheral physiology inspection apparatus of smart phone in accordance with the third embodiment of the present invention. As shown in FIG. 3, the earphone-type physiology sensing unit includes: at least one earphone main body 3014, a light emitting element 3015, and a light receiving element 3016.

The light emitting element 3015 is disposed on the earphone main body 3014 for emitting a reference light. The light receiving element 3016 is disposed on the earphone main body 3014 for receiving the reference light reflected by ear cavity skin of a human body.

The light emitting element 3015 is not limited to any sorts of light emitting element, whereas the light emitting element 3015 in the peripheral physiology inspection apparatus of smart phone in accordance with the third embodiment of the present invention is preferably a pulse oximetry LED capable of emitting 2-3 light sources with different wavelength. Moreover, the light receiving element 3016 is, but not limited to, a light sensor in the peripheral physiology inspection apparatus of smart phone in accordance with the third embodiment of the present invention. The number of the earphone main body 3014 is at least to be one and, in this embodiment, there are two earphone main bodies 3014.

In use of the peripheral physiology inspection apparatus of smart phone in accordance with the third embodiment of the present invention, the earphone main body 3014 is disposed in a user's ear cavity. Then, the light emitting element 3015 emits a reference light with a specific wavelength. This reference light is preferably an infrared or a near infrared and, in this embodiment, the reference light is an infrared.

The infrared penetrates the user's ear cavity skin and enters into the user's body tissue, and a portion of the infrared is reflected back. After that, the aforementioned light receiving element 3016 receives the infrared reflected from the human body, and thus the oximetry can be evaluated via the ratio of incident light and reflective light. The evaluation of oximetry and pulse by optical signal is well known to those skilled in the art, and thus a detail description about the implementation thereof is deemed unnecessary. Moreover, the delivery and the transformation of the physiology signal in the peripheral physiology inspection apparatus of smart phone in accordance with the third embodiment of the present invention are the same as those of the second and thus a detailed description therefor is also deemed unnecessary.

Embodiment 4

Figure 4:
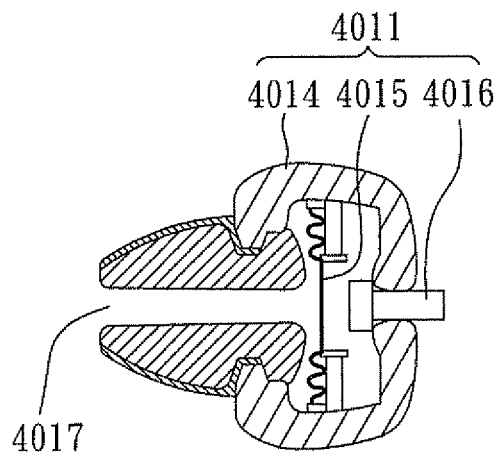
FIG. 4 is a schematic view illustrating the peripheral physiology inspection apparatus of smart phone in accordance with the fourth embodiment of the present invention.

The peripheral physiology inspection apparatus of smart phone in accordance with the fourth embodiment of the present invention is similar to that in accordance with the second embodiment of the present invention, except for the structure of the first physiology sensing unit. The first physiology sensing unit 4011 of this embodiment is also an earphone-type first physiology sensing unit. As shown in FIG. 4, which is a schematic view illustrating the peripheral physiology inspection apparatus of smart phone in accordance with the fourth embodiment of the present invention, the earphone-type first physiology sensing unit includes: at least one earphone main body 4014, an infrared transparent drum membrane 4015, and an NIR sensing element 4016.

Additionally, as shown in FIG. 4, the earphone main body 4014 has a channel space 4017, and the infrared transparent drum membrane 4015 is disposed inside the earphone main body 4014 for facing the channel space 4017. Furthermore, the NIR sensing element 4016 is disposed inside the earphone main body 4014 for facing the channel space 4017 through the infrared transparent drum membrane 4015.

In use of the peripheral physiology inspection apparatus of smart phone in accordance with the fourth embodiment of the present invention, the earphone main body 4014 is disposed in a user's ear cavity. After that, the electromagnetic radiation (i.e., NIR light) radiated by the human body passes through the channel space 4017 and penetrates the infrared transparent drum membrane 4015. Then, the electromagnetic radiation is received by the NIR sensing element 4016, and thus the temperature of the user can be measured by the peripheral physiology inspection apparatus of smart phone in accordance with the fourth embodiment of the present invention.

Measuring the temperature of a human body by electromagnetic radiation is well known to those skilled in the art, and thus a detailed description about the implementation thereof is deemed unnecessary. Moreover, the delivery and the transformation of the physiology signal in the peripheral physiology inspection apparatus of smart phone in accordance with the third embodiment of the present invention are the same as those of the second and thus a detailed description therefor is also deemed unnecessary.

Embodiment 5

Figure 5:
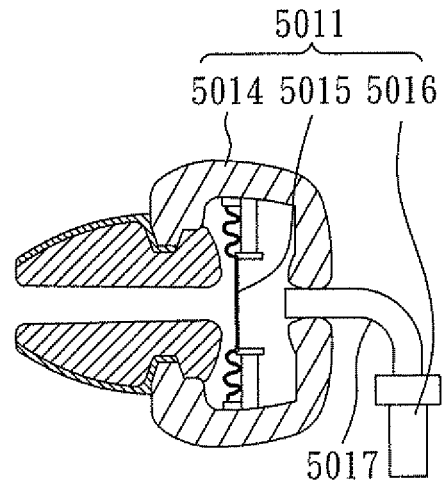
FIG. 5 is a schematic view illustrating the peripheral physiology inspection apparatus of smart phone in accordance with the fifth embodiment of the present invention.

The peripheral physiology inspection apparatus of smart phone in accordance with the fifth embodiment of the present invention is similar to that in accordance with the fourth embodiment of the present invention, except that the earphone-type physiology sensing unit in the peripheral physiology inspection apparatus of smart phone in accordance with the fifth embodiment of the present invention further includes a fiber for allowing the overall design of the peripheral physiology inspection apparatus to be smaller and more aesthetic. With reference to FIG. 5, FIG. 5 is a schematic view illustrating the peripheral physiology inspection apparatus of smart phone in accordance with the fifth embodiment of the present invention. As shown, the first physiology sensing unit 5011 is also an earphone-type physiology sensing unit in the peripheral physiology inspection apparatus of smart phone in accordance with the fifth embodiment of the present invention, and the earphone-type physiology sensing unit includes: at least one earphone main body 5014, an infrared transparent drum membrane 5015, and an NIR sensing element 5016.

In addition, a fiber 5017 is connected with the earphone main body 5014 and the NIR sensing element 5016. Therefore, the electromagnetic radiation as described in the fourth embodiment of the present invention is guided into the NIR sensing element 5016 through the fiber 5017.

Based on the peripheral physiology inspection apparatus of smart phone in accordance with the fifth embodiment of the present invention, the size of the earphone main body 5014 can be decreased for allowing a user to carry with more convenience as the NIR sensing element 5016 is to be connected by the fiber 5017 instead of being disposed on the earphone main body 5014. Other implementations of this embodiment are the same as those of the fourth embodiment and thus a detailed description is deemed unnecessary. Besides, the delivery and the transformation of the physiology signal in the peripheral physiology inspection apparatus of smart phone in accordance with the fifth embodiment of the present invention is the same as those of the second and thus a detailed description therefor is also deemed unnecessary.

Embodiment 6

Figure 6:
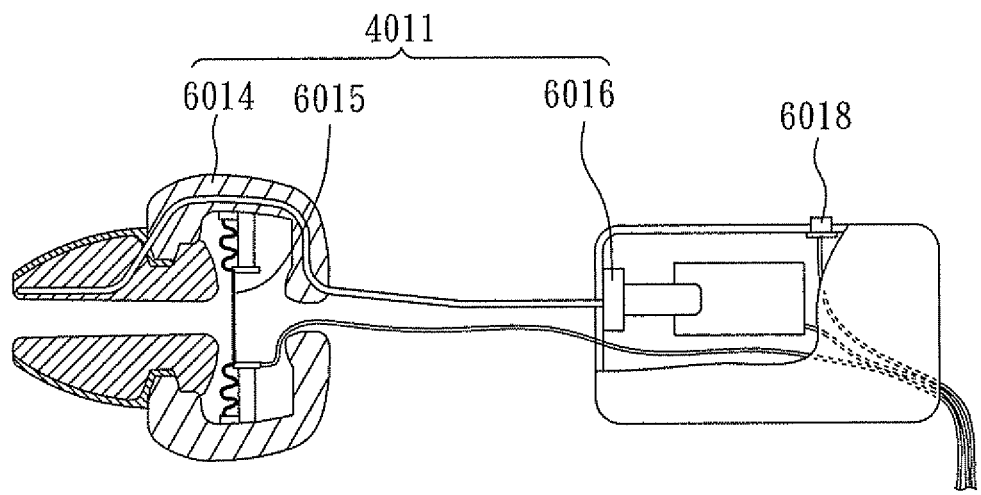
FIG. 6 is a schematic view illustrating the peripheral physiology inspection apparatus of smart phone in accordance with the sixth embodiment of the present invention.

The peripheral physiology inspection apparatus of smart phone in accordance with the sixty embodiment of the present invention is similar to that in accordance with the fifth embodiment of the present invention, except that the NIR sensing element of the earphone-type physiology sensing unit in the peripheral physiology inspection apparatus of smart phone in accordance with the sixth embodiment of the present invention is integrated with a microphone. With reference to FIG. 6, FIG. 6 is a schematic view illustrating the peripheral physiology inspection apparatus of smart phone in accordance with the sixth embodiment of the present invention. The earphone-type physiology sensing unit includes: at least one earphone main body 6014, an infrared transparent drum membrane 6015, and an NIR sensing element 6016.

Additionally, a fiber 6017 is connected with the earphone main body 6014 and the NIR sensing element 6016. Moreover, the earphone-type physiology sensing unit further has a microphone 6018, and the NIR sensing element 6016 is integrated to the microphone 6018. Therefore, in use of the peripheral physiology inspection apparatus of smart phone in accordance with the sixth embodiment of the present invention, to inspect physiology signal and to use ordinary function of the earphone (such as listen to the radio or to speak through the microphone) can be done at the same time, so as to increase the convenience of the peripheral physiology inspection apparatus of smart phone in accordance with the sixth embodiment of the present invention. Other implementations of the present sixth embodiment are the same as those of the fifth embodiment and thus a detailed description is deemed unnecessary. Besides, the delivery and the transformation of the physiology signal in the peripheral physiology inspection apparatus of smart phone in accordance with the sixth embodiment of the present invention are the same as those of the second embodiment and thus a detailed description therefor is also deemed unnecessary.

Embodiment 7

Figure 7A:
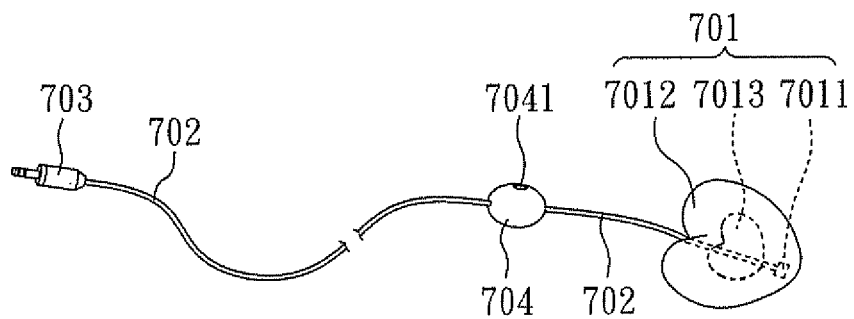
FIG. 7A is a perspective view illustrating the peripheral physiology inspection apparatus of smart phone in accordance with the seventh embodiment of the present invention.

With reference to FIG. 7A, FIG. 7A is a perspective view illustrating the peripheral physiology inspection apparatus of smart phone in accordance with the seventh embodiment of the present invention. As shown in FIG. 7A, the inspection main body 701 includes a first physiology sensing unit 7011 and a second physiology sensing unit 7012, wherein the second physiology sensing unit 7012 is of a heart shape and the first physiology sensing unit 7011 is disposed inside the second physiology sensing unit 7012. Furthermore, an electrode plate 7013 is disposed on the second physiology sensing unit 7012, and the electrode plate 7013 also has a heart shape for corresponding to the shape of the second physiology sensing unit 7012.

It is noted that, because the shapes of both the second physiology sensing unit 7012 and the electrode plate 7013 are the same and corresponding to each, the appearance of the peripheral physiology inspection apparatus of smart phone in accordance with the second embodiment of the present invention can be made to be more aesthetic. However, the shapes of the two elements are not limited to hear shape.

Figure 7B:
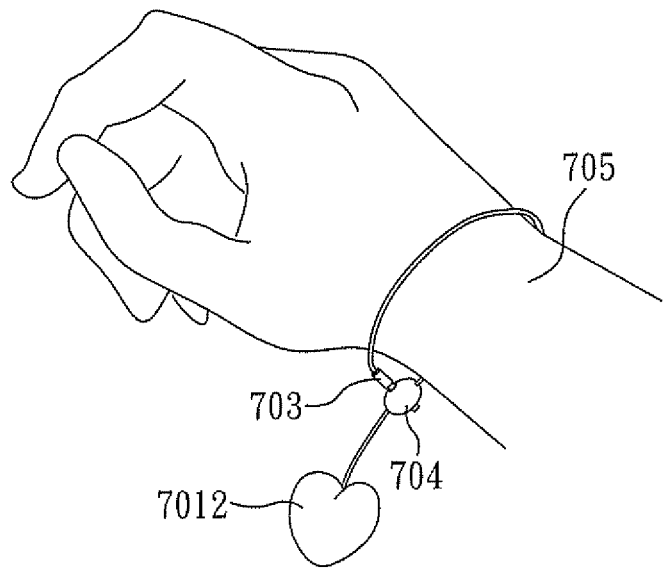
FIG. 7B is another perspective view illustrating the peripheral physiology inspection apparatus of smart phone in accordance with the seventh embodiment of the present invention.

Furthermore, the first physiology sensing unit 7011 is linked with a signal transmission unit 702 for connecting to outside and, a TRRS terminal 703 is provided on the other side of the signal transmission unit 702. With reference to FIG. 7B, FIG. 7B is another perspective s view illustrating the peripheral physiology inspection apparatus of smart phone in accordance with the seventh embodiment of the present invention. It is known that, from FIG. 7B and the above description, the peripheral physiology inspection apparatus is formed into a closed shape by way of an accommodation element 704 comprised in the peripheral physiology inspection apparatus. Furthermore, an accommodation opening 7041 is opened on the accommodation element 704 for receiving the TRRS terminal 703. Therefore, the peripheral physiology inspection apparatus of smart phone in accordance with the seventh embodiment of the present invention turns into a bracelet-type physiology inspection apparatus. This bracelet-type physiology inspection apparatus can be worn on a user, such as to sleeve it onto the user's wrist 705, for promoting the convenience to the peripheral physiology inspection apparatus of smart phone in accordance with the seventh embodiment of the present invention.

Figure 7C:
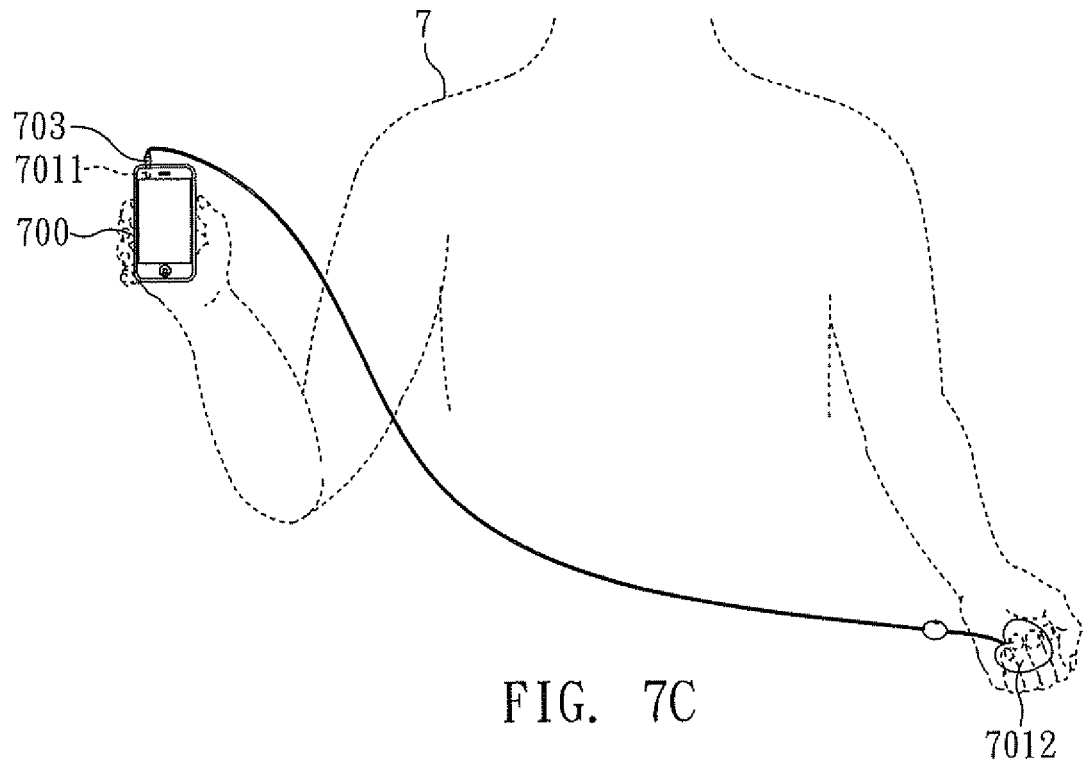
FIG. 7C is a schematic view illustrating the use of the peripheral physiology inspection apparatus of smart phone in accordance with the seventh embodiment of the present invention.

Moreover, with reference to FIG. 7C, which is a schematic view illustrating the use of the peripheral physiology inspection apparatus of smart phone in accordance with the seventh embodiment of the present invention, the peripheral physiology inspection apparatus is used with a smart phone 700 in the peripheral physiology inspection apparatus of smart phone in accordance with the seventh embodiment of the present invention. The smart phone 700 has a TRRS socket 7001 for allowing the aforementioned TRRS terminal 703 to be inserted thereinto correspondingly. Furthermore, an electrode plate (not shown) is disposed at the rear side of the smart phone 700.

As shown in FIG. 7C, when a user 7 uses the peripheral physiology inspection apparatus of smart phone in accordance with the seventh embodiment of the present invention, the second physiology sensing unit 7012 is held by one hand of the user and the smart phone 700 is held by the other hand. That is, both hands of the user 7 touch with the electrode plate 7013 on the second physiology sensing unit 7012 and the electrode plate at the rear side of the smart phone 700 respectively, so as to form a loop. Thus, the user's heartbeat physiology signal can be inspected by the peripheral physiology inspection apparatus of smart phone in accordance with the seventh embodiment of the present invention. This physiology signal is further delivered to the smart phone 700 for analysis thereby acquiring the EKG of the user 7.

Figure 7D:
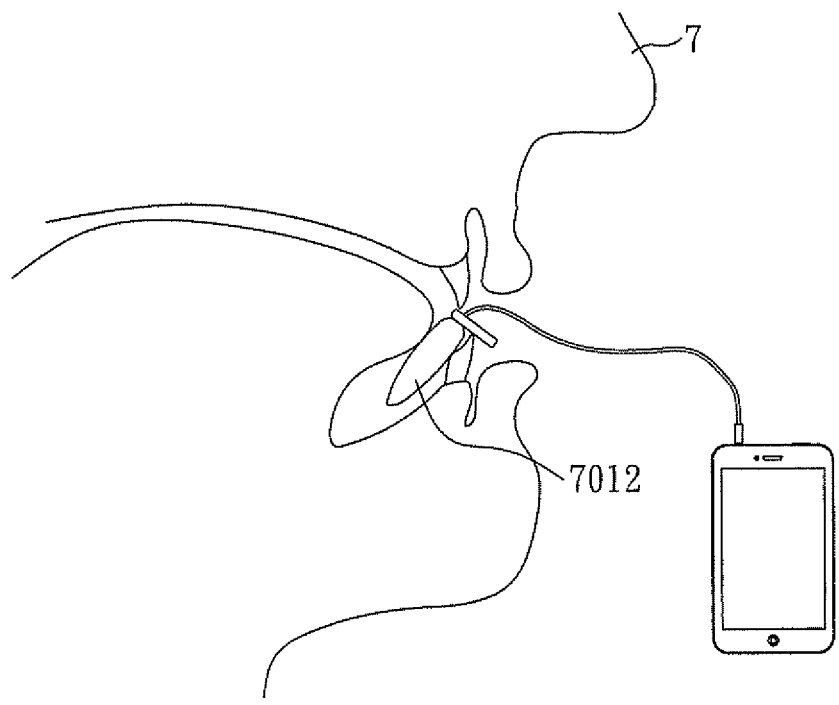
FIG. 7D is another schematic view illustrating the use of the peripheral physiology inspection apparatus of smart phone in accordance with the seventh embodiment of the present invention.

Additionally, the second physiology sensing unit 7012 is an oral-type physiology sensing unit in the peripheral physiology inspection apparatus of smart phone in accordance with the seventh embodiment of the present invention. With reference to FIG. 7D, which is another schematic view illustrating the use of the peripheral physiology inspection apparatus of smart phone in accordance with the seventh embodiment of the present invention. When the peripheral physiology inspection apparatus of smart phone in accordance with the seventh embodiment of the present invention is used, the second physiology sensing unit 7012 is put in the mouth of the user 7. The first physiology sensing unit 7011 is integrated with multiple physiology sensing units for inspecting the temperature and the saliva of the user. By this, the user's physiology signal can be obtained from the saliva of the user 7, so as to inspect the ovulation status of the user. Accordingly, it is able to benefit females in taking control of ovulation status, safe period, and physiology status preciously through saliva inspection, thereby helping with controlling contraception and fertility.

Moreover, to inspect ovulation by saliva and mouth temperature is well known to those skilled in the art, and thus a detailed description about the implementation thereof is deemed unnecessary. In addition, the delivery and the transformation of the physiology signal in the peripheral physiology inspection apparatus of smart phone in accordance with the seventh embodiment of the present invention are the same as those of the second embodiment and thus a detailed description therefor is also deemed unnecessary.

Embodiment 8

Figure 8A:
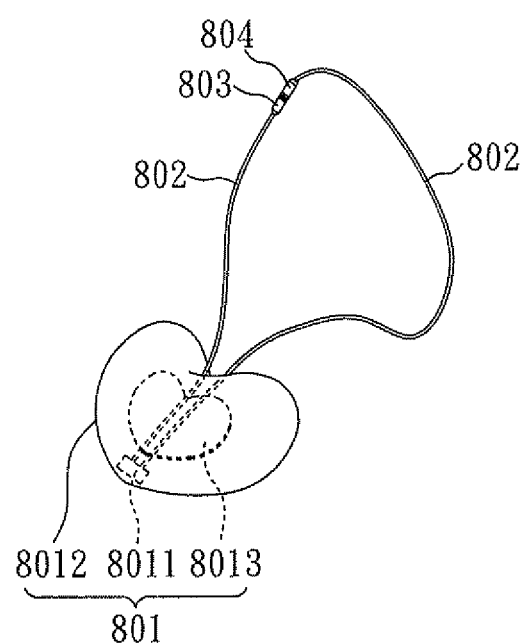
FIG. 8A is a schematic view illustrating the peripheral physiology inspection apparatus of smart phone in accordance with the eighth embodiment of the present invention.

With reference to FIG. 8A, FIG. 8A is a schematic view illustrating the peripheral physiology inspection apparatus of smart phone in accordance with the eighth embodiment of the present invention. As shown in FIG. 8A, in this embodiment, the inspection main body 801 includes a first physiology sensing unit 8011 and a second physiology sensing unit 8012, and the second physiology sensing unit 8012 is of a heart shape. Furthermore, the first physiology sensing unit 8011 is disposed inside the second physiology sensing unit 8012. In addition, an electrode plate 8013 is disposed on the second physiology sensing unit 8012, and the electrode plate 8013 also has a heart shape for corresponding to the shape of the second physiology sensing unit 8012.

It is noted that, because the shapes of both the second physiology sensing unit 8012 and the electrode plate 8013 are the same and corresponding to each other, the appearance of the peripheral physiology inspection apparatus of smart phone in accordance with the second embodiment of the present invention can be made to be more aesthetic. However, the shapes of the two elements are not limited to hear shape.

Furthermore, the first physiology sensing unit 8011 is linked with two signal transmission units 802 for connecting to outside. A TRRS terminal 803 is provided at an end of one of the two signal transmission units 802, and a TRRS terminal receiver 804 is provided at an end of the other signal transmission unit 802. Additionally, as shown in FIG. 8A, the TRRS terminal 803 and the TRRS terminal receiver 804 are jointed correspondingly. Therefore, the peripheral physiology inspection apparatus of smart phone in accordance with the eighth embodiment of the present invention forms a necklace-type peripheral physiology inspection apparatus. This necklace-type peripheral physiology inspection apparatus can be worn on a user, such as to hang on the neck of the user, for promoting the convenience to the peripheral physiology inspection apparatus of smart phone in accordance with the eighth embodiment of the present invention.

Additionally, the second physiology sensing unit 8012 is an oral-type physiology sensing unit in this embodiment. When the peripheral physiology inspection apparatus of smart phone in accordance with the eighth embodiment of the present invention is used, the second physiology sensing unit 8012 is put in the mouth of the user (as shown in FIG. 7D). By this, the user's physiology signal can be obtained from the saliva of the user 7, so as to inspect the ovulation status of the user. Accordingly, it is able to benefit females in taking control of ovulation status, safe period, and physiology status preciously through saliva inspection, thereby helping with controlling contraception and fertility.

Figure 8B:
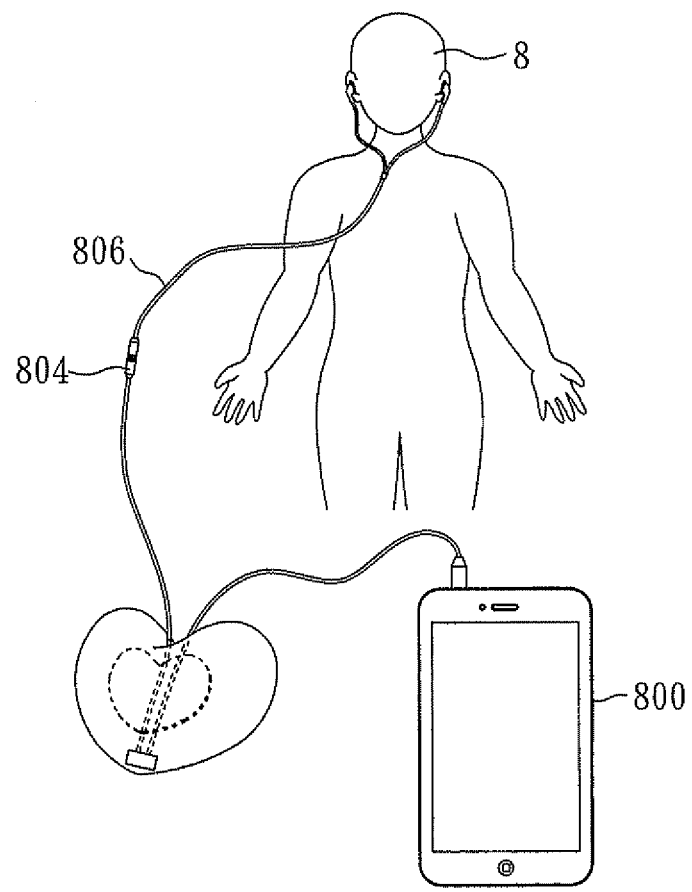
FIG. 8B is a schematic view illustrating the use of the peripheral physiology inspection apparatus of smart phone in accordance with the eighth embodiment of the present invention.

With reference to FIG. 8B, FIG. 8B is a schematic view illustrating the use of the peripheral physiology inspection apparatus of smart phone in accordance with the eighth embodiment of the present invention. As shown in FIG. 8B, when the peripheral physiology inspection apparatus of smart phone in accordance with the eighth embodiment of the present invention is used, the aforementioned TRRS terminal 803 is connected with a smart phone 800, and the aforementioned TRRS terminal receiver 804 can be further connected with an earphone with a TRRS terminal, so as to allow the user 8 to listen to music and to inspect physiology signal at the same time.

To inspect ovulation by saliva and mouth temperature is well known to those skilled in the art, and thus a detailed description about the implementation thereof is deemed unnecessary.

Besides, the peripheral physiology inspection apparatus of smart phone in accordance with the eighth embodiment of the present invention can further be combined with the earphone-type physiology sensing unit as described in the second embodiment of the present invention. The user 8 can thus put the earphone-type physiology sensing unit as described in the second embodiment of the present invention in the ear cavity, so that the conductive surface 2015 of the earphone main body 2014 comes into touch with the ear cavity skin of the user for forming a first contact, and a second contact is further formed by making any part of the body of the user 8 come into touch with the electrode plate 8013 of the second physiology sensing unit 8012 (as the manner to form the second contact described in the second embodiment 2), thereby forming an inspection loop for inspecting the EKG of the user 8.

Furthermore, the delivery and the transformation of the physiology signal in the peripheral physiology inspection apparatus of smart phone in accordance with the eighth embodiment of the present invention are the same as those of the second embodiment and thus a detailed description is deemed unnecessary.

Embodiment 9

Figure 9:
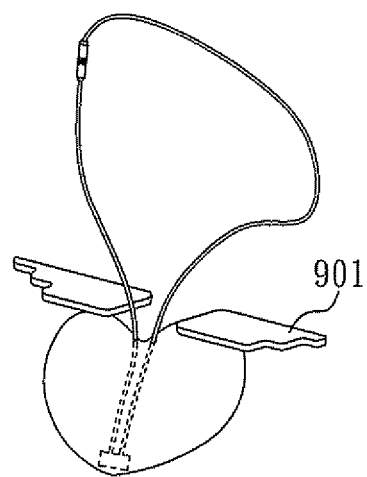
FIG. 9 is a perspective view illustrating the peripheral physiology inspection apparatus of smart phone in accordance with the ninth embodiment of the present invention.

With reference to FIG. 9, FIG. 9 is a perspective view illustrating the peripheral physiology inspection apparatus of smart phone in accordance with the ninth embodiment of the present invention. The peripheral physiology inspection apparatus of smart phone in accordance with the ninth embodiment of the present invention is similar to that in accordance with the eighth embodiment of the present invention, except that the second physiology sensing unit of the peripheral physiology inspection apparatus of smart phone in accordance with the ninth embodiment of the present invention further has an auxiliary element 901.

As shown in FIG. 9, the auxiliary element 901 has a wing shape. The auxiliary element 901 in wing shape is made to prettify the appearance of the peripheral physiology inspection apparatus of smart phone in accordance with the ninth embodiment of the present invention. In addition, the user can hold the peripheral physiology inspection apparatus of smart phone in accordance with the ninth embodiment of the present invention in the mouth easily by biting the auxiliary element 901. It is noted that other implementations of the peripheral physiology inspection apparatus of smart phone in accordance with the ninth embodiment of the present invention are the same as those in accordance with the eighth embodiment of the present invention, and hence the related description is omitted.

Embodiment 10

Figure 10A:
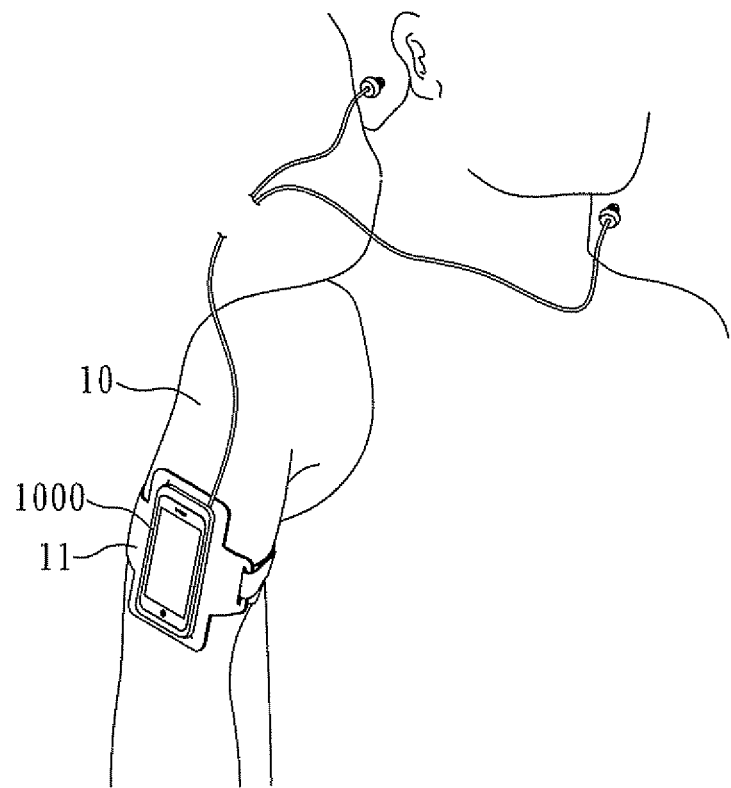
FIG. 10A is a perspective view illustrating the peripheral physiology inspection apparatus of smart phone in accordance with the tenth embodiment of the present invention.

With reference to FIG. 10A, FIG. 10A is a perspective view illustrating the peripheral physiology inspection apparatus of smart phone in accordance with the tenth embodiment of the present invention. The peripheral physiology inspection apparatus of smart phone in accordance with the tenth embodiment of the present invention is similar to that of the previous embodiments, and thus those skilled in the art can accomplish this embodiment with reference to the previous embodiments.

As shown in FIG. 10A, similar to the description in the previous embodiment, a smart phone 1000 is disposed on the arm of a user 10 by a fixing element 11. Moreover, an electrode plate (not shown) is disposed at the rear side of the smart phone 1000.

As aforementioned, the earphone-type physiology sensing unit described in the second embodiment can be accompanied with the mobile phone 1000, and the earphone-type physiology sensing unit and the smart phone 1000 are connected with each other by a TRRS terminal.

Furthermore, a first contact is formed due to the touching between the conductive surface 2015 of the earphone main body 2014 and the skin inside of the ear cavity of the user. Moreover, a second contact is formed due to the touching between the electrode plate at the rear side of the smart phone 1000 and the skin of the user's arm, thereby forming an inspection loop. By this, the user's EKG can be measured. It is noted that the formation of the second contact is not limited to touching between the skin of the user's arm and the smart phone 1000. Another alternative is to have a touching between the skin of the user's abdomen and the smart phone 1000.

However, EKG signal is weak and thus likely to be interfered by external noise (such as electromagnetic wave from a mobile phone) or background noise (such as circuit noise). Thus, it is preferred to adjust the contacting positions of the first and the second contacts, for allowing the heart of the user to be in between the two electrode contacts (as shown in FIG. 10A). By this, a stronger EKG signal is acquired and the efficiency of EKG inspection is thus increased.

It is noted that the electrode sheet can be a metal conductive film or a non-metal conductive film as described in the second embodiment. The electrode sheet can be a conductive silver paint, conductive polymer, a platinum, conductive polymerizing cyclic, or metal ring, wherein the electrode sheet is a metal ring in the tenth embodiment of the present invention.

Figure 10B:
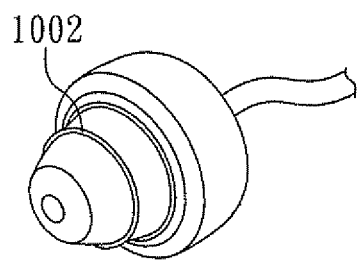
FIG. 10B is a perspective view illustrating the earphone main body of the peripheral physiology inspection apparatus of smart phone in accordance with the eighth embodiment of the present invention.

With reference to FIG. 10B, FIG. 10B is a perspective view illustrating the earphone main body of the peripheral physiology inspection apparatus of smart phone in accordance with the tenth embodiment of the present invention. As shown in FIG. 10B, the metal ring is disposed on the earphone main body, so that the amount of material for producing the metal ring is decreased. Moreover, the delivery and the transformation of the physiology signal in the peripheral physiology inspection apparatus of smart phone in accordance with the tenth embodiment of the present invention are the same as those of the previous embodiments and thus a detailed description is deemed unnecessary.

Embodiment 11

Figure 11:
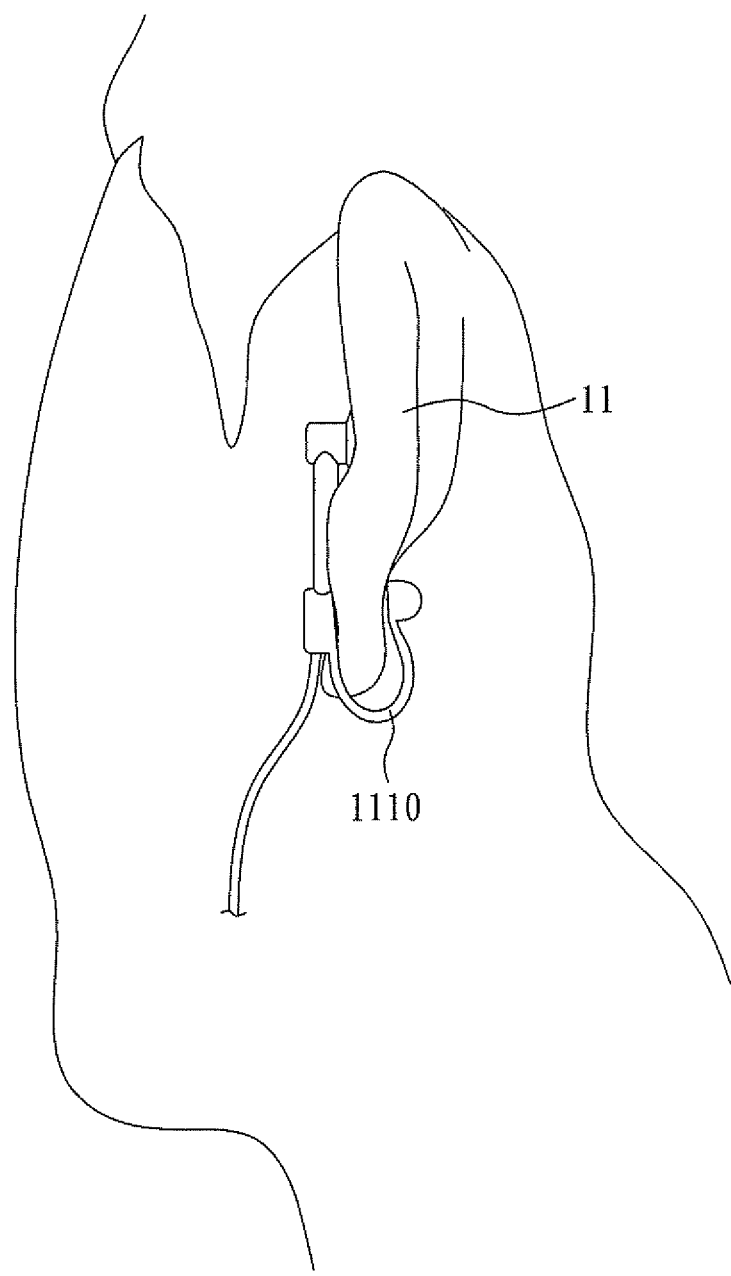
FIG. 11 is a schematic view illustrating the peripheral physiology inspection apparatus of smart phone in accordance with the eleventh embodiment of the present invention.

With reference to FIG. 11, FIG. 11 is a schematic view illustrating the peripheral physiology inspection apparatus of smart phone in accordance with the eleventh embodiment of the present invention. The peripheral physiology inspection apparatus of smart phone in accordance with the eleventh embodiment of the present invention is similar to that of the previous embodiments, and thus those skilled in the art can accomplish this embodiment with reference to the previous embodiments.

As shown in FIG. 11, similar to the description in the previous embodiment, an earphone-type physiology sensing unit is disposed in the ear cavity of a user 11, so as to fox in a physical contact by gripping the earlobe with a eardrop-like structure, for assisting measurement of EKG and EEG and for promoting aesthetic appearance as well. Furthermore, the earphone-type physiology sensing unit further includes a carotid artery sensing element 1110, which is disposed at a position close to the carotid arteries of the user 11, for inspecting the user's heart sound. The heart sound physiology signal is then sent to a smart phone connected with the peripheral physiology inspection apparatus of smart phone in accordance with the present eleventh preferred embodiment for signal processing for analysis. Moreover, the delivery and the transformation of the physiology signal in the peripheral physiology inspection apparatus of smart phone in accordance with the eleventh embodiment of the present invention are the same as those of the previous embodiments and thus a detailed description is deemed unnecessary.

Embodiment 12

Figure 12:
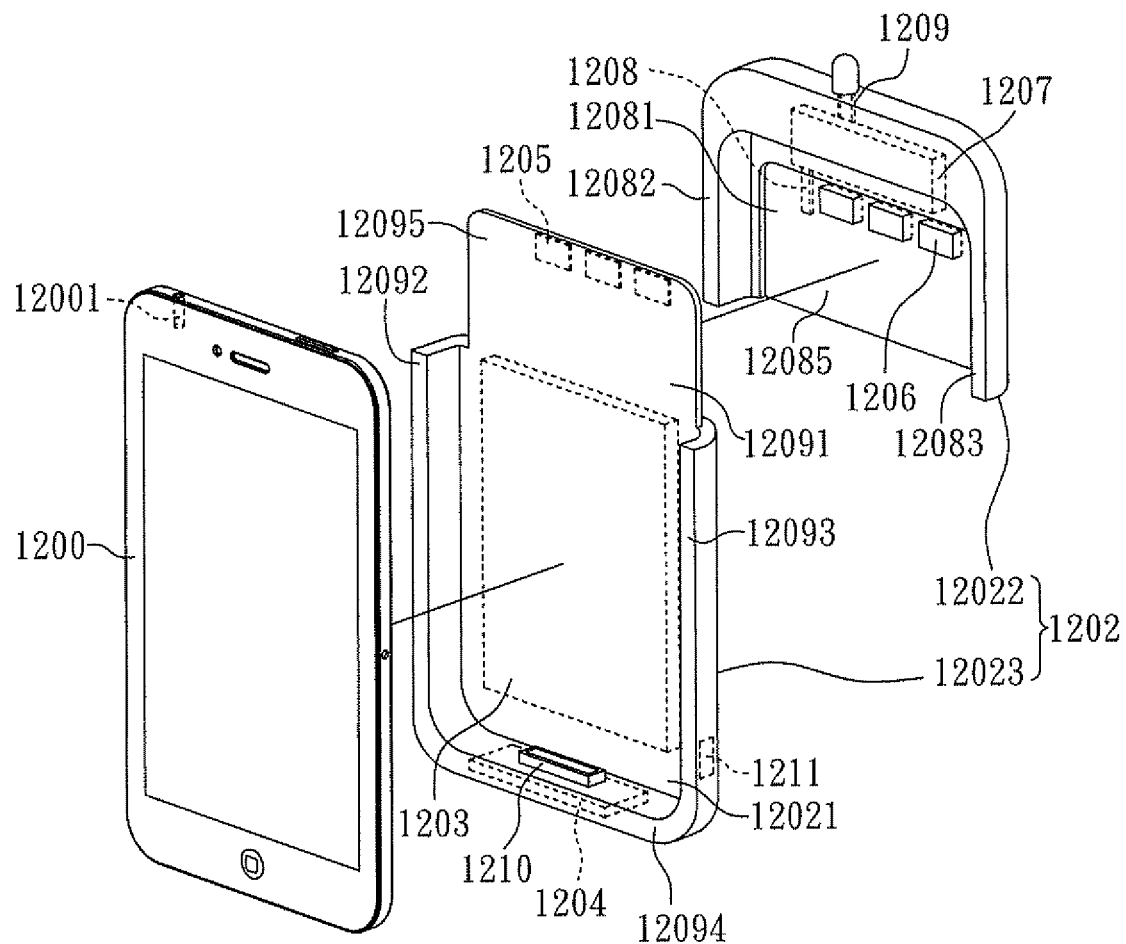
FIG. 12 is a schematic view illustrating the peripheral auxiliary apparatus of smart phone in accordance with the twelfth embodiment of the present invention

With reference to FIG. 12, FIG. 12 is a schematic view illustrating the peripheral auxiliary apparatus of smart phone in accordance with the twelfth embodiment of the present invention. As shown in FIG. 12, the peripheral auxiliary apparatus of smart phone in accordance with the twelfth embodiment of the present invention is for use with a smart phone 1200 having a TRRS socket 12001. The peripheral auxiliary apparatus includes: a shell 1202, a battery unit 1203, a power management unit 1204, a first conductive unit 1205, a second conductive unit 1206, and a signal conversion unit 1207.

The shell 1202 has a receiving part 12021, a TRRS terminal 1208, and a TRRS terminal receiver 1209. The receiving part 12021 is provided for receiving the smart phone 1200.

Moreover, the battery unit 1203 is disposed inside the shell 1202, and the power management unit 1204 is electrically connected to the battery unit 1203. Furthermore, the first conductive unit 1205 is disposed on the shell 1202, and the second conductive unit 1206 is disposed on the shell 1202 for contacting the first conductive unit 1205 correspondingly. The second conductive unit 1206 is electrically connected to the power management unit 1204.

The signal conversion unit 1207 is disposed in the shell 1202 and electrically connected to the first conductive unit 1205. The TRRS terminal 1208 and the TRRS terminal receiver 1209 are electrically connected with the signal conversion unit 1207, and the TRRS terminal 1208 is inserted into the TRRS socket 12001 of the smart phone 1200 correspondingly.

It is noted that the aforementioned shell 1202 includes an upper shell 12022 and a lower shell 12023. The upper shell 12022 and the lower shell 12023 are combined correspondingly to form the receiving part 12021. Moreover, the upper shell 12022 and the lower shell 12023 are combined by wedging with each other. However, the combination of the upper shell 12022 and the lower shell 12023 is not limited to the above manner; for example, the upper shell 12022 and the lower shell 12023 or can be combined or separated through a sliding rail apparatus. Besides, the shell 1202 is not limited to be composed of the upper shell 12022 and the lower shell 12023; for example, the shell 1202 can be formed as an integral structure, which implies that the shell 1202 is formed into a one-piece structure.

Moreover, as shown in FIG. 12, the lower shell 12023 includes a back plate 12091 that is of a rectangular shape. Furthermore, the back plate 12091 has two side edges 12092, 12093 and a bottom edge 12094. The two side edges 12092, 12093 are extended from the two long edges of the back plate 1209, and the bottom edge 12094 is extended from one of the short edges of the back plate 1209, and connected with the two side edges 12092, 12093 respectively, so that the two side edges 12092, 12093 and the bottom edge 12094 define an receiving space (i.e., the receiving part 12021) for receiving the smart phone 1200.

The battery unit 1203 is a Li-polymer battery in the peripheral auxiliary apparatus of smart phone in accordance with the twelfth embodiment of the present invention. It is noted that the battery unit 1203 is not limited to Li-polymer battery. Any kinds of battery with properties of high energy-storing efficiency, small volume are suitable for the peripheral auxiliary apparatus of smart phone in accordance with the twelfth embodiment of the present invention. In addition, the battery unit 1203 has a film shape and is disposed inside the back plate 12091 for providing an extra electric power.

Additionally, as shown in FIG. 12, the power management unit 1204 is disposed inside the bottom edge 12094. The power management unit 1204 is electrically connected with the battery unit 1203 for receiving the electric power provided by the battery unit 1203, and then distributing and transforming the electric power provided by the battery unit 1203. Furthermore, a connection port 1210 is disposed on the aforementioned bottom edge 12094, wherein the connection port 1210 is a 30-pin connection port. When the smart phone 1200 is received in the receiving part 12021 correspondingly, this connection port 1210 corresponds to a connection port (not shown) of the smart phone 1200, for allowing the connection port 1210 on the bottom edge 12094 of the shell 1202 to be electrically connected with the connection port of the smart phone 1200. The connection port of the smart phone 1200 is a standard interface, which includes USB connection pins, firewall pins, and video signal pins, and so on.

Additionally, as shown in FIG. 12, the back plate 12091 has a first back plate surface 12095 disposed thereon the aforementioned first conductive unit 1205$n$. It is noted that the first conductive unit 1205 can be electrically connected with the battery unit 1203 directly, or indirectly through the power management unit 1204. In this embodiment, the first conductive unit 1205 is electrically connected with the battery unit 1203 indirectly through the power management unit 1204.

Moreover, an USB connection port 1211 is formed on any one of the two side edges 12092, 12093 in the peripheral auxiliary apparatus of smart phone in accordance with the twelfth embodiment of the present invention. The USB connection port 1211 is a mini-B type USB connection port for being electrically connected with the aforementioned USB connection pins of the connection port of the smart phone 1200. Therefore, a single USB connection port is provided when the smart phone is received in the shell.

With reference to FIG. 12 again, the upper shell 12022 includes a back plate 12081 that is of a rectangular shape. Furthermore, the back plate 12081 has two side edges 12082, 12083 and a top edge 12084. The two side edges 12082, 12083 are extended from the two long edges of the back plate 12081, and the top edge 12084 is extended from one of the short edge of the back plate 12081, and connected with the two side edges 12082, 12083 respectively, so that the two side edges 12082, 12083 and the top edge 12084 define an receiving space (i.e., the receiving part 12021) for receiving the smart phone 1200.

Additionally, the back plate 12081 has a first back plate surface 12085 disposed thereon the aforementioned second conductive unit 1206. The first conductive unit 1205 and the second conductive unit 1206 are contacted with each other when the upper shell 12022 and the lower shell 12023 are combined correspondingly. Therefore, a transmission path is formed due to the contact between the first conductive unit 1205 and the second conductive unit 1206.

Furthermore, the aforementioned signal conversion unit 1207 is disposed in the top edge 12084, and it is noted that the signal conversion unit 1207 is electrically connected with the second conductive unit 1206. Hence, the signal conversion unit 1207 can obtain the electric power provided by the battery unit 1203 through the second conductive unit 1206, the first conductive unit 1205, and the power management unit 1204, thereby allowing the signal conversion unit 1207 to operate normally.

With reference to FIG. 12 again, the TRRS terminal 1208 and the TRRS terminal receiver 1209 are disposed inside the top edge 12084. Moreover, the TRRS terminal 1208 and the TRRS terminal receiver 1209 are electrically connected with the signal conversion unit 1207 respectively. It is also noted that the TRRS terminal 1208 is inserted into the TRRS socket 12001 of the smart phone 1200 correspondingly when the upper shell 12022 and the lower shell 12023 are combined correspondingly for receiving the smart phone 1200.

In summary, an electronic apparatus with a TRRS terminal can be connected with the smart phone 1200 having the aforementioned features. That is, the TRRS terminal of the electronic apparatus is inserted into the TRRS terminal receiver 1209 of the peripheral auxiliary apparatus, and a signal (such as physiology signal inspected by the electronic apparatus) is delivered to the smart phone 1200 through the signal conversion unit 1207 and the TRRS terminal 1208.

According to the peripheral auxiliary apparatus of smart phone in accordance with the twelfth embodiment of the present invention, a signal received by the signal conversion unit 1207 is converted into an audio signal.

It is noted that the features described in the first to the twelfth embodiments are not limited to be implemented in those particular embodiments. Those skilled in the art may combine the features as suggested in the above embodiments arbitrarily based on their requirements for performing different physiology signal inspections. Moreover, it is noted that the spirit of the present invention is to integrate a physiology inspection apparatus and a smart phone, wherein the physiology inspection apparatus and the smart phone are connected through a TRRS terminal.

Based on the above spirit, the integration of the physiology inspection apparatus with an earphone is further popularized by the present invention, for promoting the convenience of users. Furthermore, base on the above spirit, turning the physiology inspection apparatus of the present invention into a necklace-type, or into a bracelet-type physiology inspection apparatus is further popularized by the present invention, for promoting the convenience of users.

In the present invention, the peripheral physiology inspection apparatus is provided with powerful functionality that can inspect EKG, EEG, temperature, or other physiology signal as described in the above first to twelfth embodiments. Additionally, the peripheral physiology inspection apparatus of the present invention has aesthetic appearance, and is convenient to carry around, which provides high convenience for users who use the peripheral physiology inspection apparatus.

Although the present invention has been explained in relation to its preferred embodiment, it is to be understood that many other possible modifications and variations can be made without departing from the spirit and scope of the invention as hereinafter claimed.

What is claimed is:

1. A peripheral physiology inspection apparatus of smart phone, which is connected with a smart phone having a TRRS socket for performing a physiology inspection, the peripheral physiology inspection apparatus comprising:
   an inspection main body including a first physiology sensing unit, a second physiology sensing unit disposed on a switch, and an electrode plate disposed on the second physiology sensing unit;
   a plurality of signal transmission units; and
   a TRRS terminal for connecting with the inspection main body via the signal transmission units, the TRRS terminal being corresponding to the TRRS socket for allowing the inspection main body to be electrically connected to the smart phone, thereby enabling the smart phone to analyze and process physiology signals inspected by and delivered from the inspection main body,
   wherein the first and the second physiology sensing units are connected with each other by the signal transmission units;
   wherein the first physiology sensing unit is an earphone-type physiology sensing unit comprising:
   at least one earphone main body defined therein a channel space;
   an infrared transparent drum membrane disposed inside the earphone main body and facing to the channel space;
   an NIR sensing element disposed inside the earphone main body and facing to the channel space through the infrared transparent drum membrane; and
   a fiber for connecting the earphone main body to the NIR sensing element.

2. The peripheral physiology inspection apparatus of smart phone as claimed in claim 1, further comprising a signal conversion interface disposed between the inspection main body and the smart phone for converting the physiology signal inspected by the inspection main body into an audio signal, so as to allow the smart phone to receive the audio signal through the TRRS socket.

* * * * *